United States Patent
Helenowski

(10) Patent No.: US 7,302,037 B1
(45) Date of Patent: Nov. 27, 2007

(54) ROTATING GAMMA SYSTEM VISUAL INSPECTION CAMERA

(76) Inventor: Tomasz K Helenowski, 936 Burnham Ct., Glenview, IL (US) 60025-4140

( * ) Notice: Subject to any disclaimer, the term of this patent is extended or adjusted under 35 U.S.C. 154(b) by 61 days.

(21) Appl. No.: 11/273,305

(22) Filed: Nov. 14, 2005

(51) Int. Cl.
*A61N 5/10* (2006.01)
(52) U.S. Cl. .......................... 378/65; 378/206
(58) Field of Classification Search ........ 378/193–197, 378/65, 205–207, 210; 600/1
See application file for complete search history.

(56) References Cited

U.S. PATENT DOCUMENTS

| | | | | |
|---|---|---|---|---|
| 4,780,898 A | * | 10/1988 | Sundqvist | 378/65 |
| 5,528,653 A | * | 6/1996 | Song et al. | 378/65 |
| 6,044,126 A | * | 3/2000 | Rousseau et al. | 378/65 |
| 6,079,876 A | * | 6/2000 | Schuetz | 378/205 |
| 2003/0219100 A1 | * | 11/2003 | Okoda | 378/102 |

* cited by examiner

*Primary Examiner*—Hoon Song
(74) *Attorney, Agent, or Firm*—Michael I. Kroll

(57) ABSTRACT

A method and system of visual inspection for use with a gamma system includes a monitoring device connected within a housing proximate to a mechanical indicator of the rotating gamma system for capturing data comprising at least one of positional and operational data associated with the mechanical indicator. A control center monitors the captured data which is provided by a communication device connected between the monitoring device and the control center. Upon display of the captured data a user is able to review, monitor and maintain operation of the gamma system.

10 Claims, 7 Drawing Sheets

ROTATING GAMMA SYSTEM VISUAL INSPECTION CAMERA

BACKGROUND OF THE INVENTION

1. Field of the Invention

The present invention relates generally to gamma systems and, more specifically, to an improvement and additional safety feature for a rotating gamma system. A rotating gamma system is an instrument for performing radiosurgery on lesions in the brain and possibly other body parts. The present invention is a live video camera and appropriate lighting mounted within the housing of the gamma system to provide visual inspection of the mechanical indicator, which cannot be viewed by an operator from the control area during the radiation process.

2. Description of the Prior Art

There are other radiation therapy devices. Typical of these is U.S. Pat. No. 4,780,898 issued to Sundqvist on Oct. 25, 1988.

Another patent was issued to Kerjean on Sep. 5, 1995 as U.S. Pat. No. 5,448,611. Yet another U.S. Pat. No. 5,528,653 was issued to Song, et al. on Jun. 18, 1996 and still yet another was issued on Jul. 16, 1996 to Shepherd, et al. as U.S. Pat. No. 5,537,452.

Another patent was issued to Kopecky on May 6, 1997 as U.S. Pat. No. 5,627,870. Yet another U.S. Pat. No. 5,757,886 was issued to Song on May 26, 1998. Another was issued to Rousseau, et al. on Mar. 28, 2000 as U.S. Pat. No. 6,044,126 and still yet another was issued on Jan. 28, 2003 to Krispel, et al. as U.S. Pat. No. 6,512,813.

U.S. Pat. No. 4,780,898

Inventor: Hans Sundqvist

Issued: Oct. 25, 1988

An arrangement in a gamma unit, comprising a large number of radiation sources (9) mounted within a radiation shield (2) and having beam channels (6, 19) directed radially from said radiation sources toward a common focal point (F), said radiation shield comprising a space adapted to accommodate the head of a patient resting on a support. The novel matter resides in that the radiation sources (9) and the beam channels (6, 19) directed radially therefrom toward the focal point are located, in relation to the diametrical plane through the opening to the space, within a zone extending to latitudes 30.degree.-45.degree., as seen from said diametrical plane.

U.S. Pat. No. 5,448,611

Inventor: Joel-Theophile Kerjean

Issued: Sep. 5, 1995

Method and gamma ray collimator for the treatment of cerebral lesions by gamma irradiation. Gamma rays from a source radiate into an annular substantially divergent path made of radiation absorbing material. At the outlet of this divergent path, ribs further absorb unwanted parasitic oblique radiation. The annular beam of radiation thus formed enters an annular substantially convergent path to exit and to converge in an area to be treated. The annular beam of gamma rays that emerges through both divergent and convergent paths has a sufficient intensity to constitute a lethal dose within a defined volume and obviates the need for long term exposure to point beams of gamma radiation.

U.S. Pat. No. 5,528,653

Inventor: Shipeng Song, et al.

Issued: Jun. 18, 1996

The present invention provides a rotator Gamma radiation unit which adapts to medical Gamma systems especially. The radiation source bodies carrying sources can rotate by 360.degree. within a radiation protection case. The trace of the radiation line forms several rotating pyramids with tops at the common focus. In this way the single successive radiation in the stationary focus manner is changed to multiple-points intermittent radiation. Therefore, while ensuring the radiation amount, it is possible to decrease the number of the radiation sources and simplify the manufacturing engineering. In this way it is possible to kill the disease tissues at the focus, and prevent the nuclear radiation line from injuring the healthy tissues outside the focus.

U.S. Pat. No. 5,537,452

Inventor: Joseph S. Shepherd et al.

Issued: Jul. 16, 1996

A radiosurgery and radiotherapy system to provide diagnostic imaging and target localization via a patient 3-D mapping means such as a CT scanner or MRI, patient positioning via a four degree of freedom of motion table, and a stereotacetic Cobalt 60 therapy unit incorporating multiple sources to therapeutically irradiate a target is provided. Methods of radiosurgery and radiotherapy utilizing the system are also provided. A combination of radiation source configuration, 360 degree rotational characteristics of the therapy unit, and table movement will allow any size and shape of target to be irradiated to therapeutic levels while decreasing radiation exposure to surrounding healthy tissue. A radiation beam catcher which captures greater than 80% and preferably greater than 90 percent of the radiation from the radiation sources is also provided.

U.S. Pat. No. 5,627,870

Inventor: Bernard Kopecky

Issued: May 6, 1997

A device for treating cerebral lesions by gamma radiation, comprising an approximately semi-spherical source-collimator assembly having a large number of gamma ray sources associated with channels directed to the same focal point. Each gamma ray source is associated with a group of channels arranged in the manner of a cone, the apex of which is at the focal point.

U.S. Pat. No. 5,757,886

Inventor: Shipeng Song

Issued: May 26, 1998

The present invention discloses a process for converting the beam diameter of radioactive rays and a radiating unit used in a medical stereotacetic radiotherapeutic apparatus.

Over a collimator base (11) symmetrical about a central axis are distributed a number set of collimators (1) of different aperture diameter. The rule of distribution of each set of collimators is the same as that of the radioactive sources (2) in the source base (4). The collimator base (11) can be rotated according to the requirement of the therapy to make a set of collimators (1) of a certain aperture diameter in alignment with the radioactive sources (2). Thus it is possible to alter the size of the beam diameter of radioactive rays. The advantages of the invention are convenience in operation, enhancement of the accuracy of positioning and the easiness of putting into practice the automatic control by a computer.

U.S. Pat. No. 6,044,126

Inventor: Jean Rousseau, et al.

Issued: Mar. 28, 2000

Process for determining the configuration or configurations [treatment time ($TT_i$)/diameter ($\phi_{i,f}$) of each collimator] of a helmet for stereotacetic radiosurgery, to which can be fitted an plurality of collimators focused on an irradiation isocenter, consisting in automatically optimizing, through iterative dose calculation, the dose ($D_p$) received at predetermined optimization points ($M_p$), by modifying, in the course of the successive iterations, the treatment time ($TT_i$) of at least one shot (i) and the diameter ($\phi_{i,f}$) of at least one collimator ($C_f$) of at least one shot (i), and by calculating, at each iteration, an objective function (OF) having as variables the differences between the calculated dose ($D_p$) and the expected dose ($ED_p$) for each point of optimization ($M_p$), iterative calculation of the doses being carried out automatically until the objective function (OF) satisfies a predetermined optimization criterion.

U.S. Pat. No. 6,512,813

Inventor: Franz Krispel, et al.

Issued: Jan. 28, 2003

A system for isometric irradiation of target tissue from multiple radiation sources includes a structure supporting an oblique array of radiation sources disposed to rotate about an axis (28) coinciding with the longitudinal axis of a patient, such that individual sources describe non-overlapping trajectories on the surface of the patient. The sources are supported by asymmetric source carrier (24) within relatively limited angular region about said axis. The sources are collimated by selectable sets of apertures (31*ai*-31*di*) arranged on mutually independently rotatable rings (30*a*-30*d*), each such ring selectably capable of alignment with a sub-array (24*a*-24*f*) of sources to produce a variety of patterns and dynamic intensity modulations of the radiation flux.

SUMMARY OF THE PRESENT INVENTION

The present invention relates generally to gamma systems and, more specifically, to an improvement and additional safety feature for a rotating gamma system. A rotating gamma system is an instrument for performing radiosurgery on lesions in the brain and possibly other body parts. The present invention is a live video camera and appropriate lighting mounted within the housing of the gamma system to provide visual inspection of the mechanical indicator, which cannot be viewed by an operator from the control area during the radiation process.

A primary object of the present invention is to provide a gamma system visual inspection device that overcomes the shortcomings of the prior art Another secondary object of the present invention is to provide a gamma system visual inspection device that allows visual inspection of the mechanical indicator in a rotating gamma system, which cannot be viewed by an operator from the control area during the radiation process.

Another object of the present invention is to provide a gamma system visual inspection device that has a video camera within the internal structure of a rotating gamma system.

Yet another object of the present invention is to provide a gamma system visual inspection device that has at least one light within the internal structure of a rotating gamma system.

Still another object of the present invention is to provide a gamma system visual inspection device wherein the video camera and lighting allows the operator to visually inspect the mechanical indicator.

Yet another object of the present invention is to provide a gamma system visual inspection device wherein the operator visually inspects the mechanical indicator from a safe control room during operation of radiation process.

Another object of the present invention is to provide a gamma system visual inspection device wherein the live video of the mechanical indicator is recorded for subsequent viewing.

Still yet another object of the present invention is to provide a gamma system visual inspection device that provides additional safety features to insure proper operation of a rotating gamma system.

Still another object of the present invention is to provide a gamma system visual inspection device that is simple and easy to use.

Another object of the present invention is to provide a gamma system visual inspection device that is inexpensive to manufacture and operate.

Additional objects of the present invention will appear as the description proceeds.

The present invention overcomes the shortcomings of the prior art by providing an improvement and additional safety feature for a rotating gamma system. The rotating gamma system is an instrument for performing radiosurgery on lesions in the brain. While in operation, there is a source carrier that rotates as well as a collimator carrier that rotates independently. The rotational positions of these two carriers is precisely controlled and monitored electronically. In addition to the electronic encoders for tracking the position of these two carriers, there is a mechanical indicator built into the machine that shows the positions of the two carriers. The mechanical indicator is located within the gamma system and cannot be viewed by an operator from the control area during the radiation process. The invention is a gamma system visual inspection device that includes live video camera and lights mounted within the back of the internal structure of the gamma system to provide visual inspection of the mechanical indicator during the radiation process. Since the mechanical indicator is not visible from the control area, the live video camera and lighting system of the present invention can observe the mechanical indicator from the control area during the operation of the machine. This would allow an additional safety feature to make sure the machine is operating properly.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
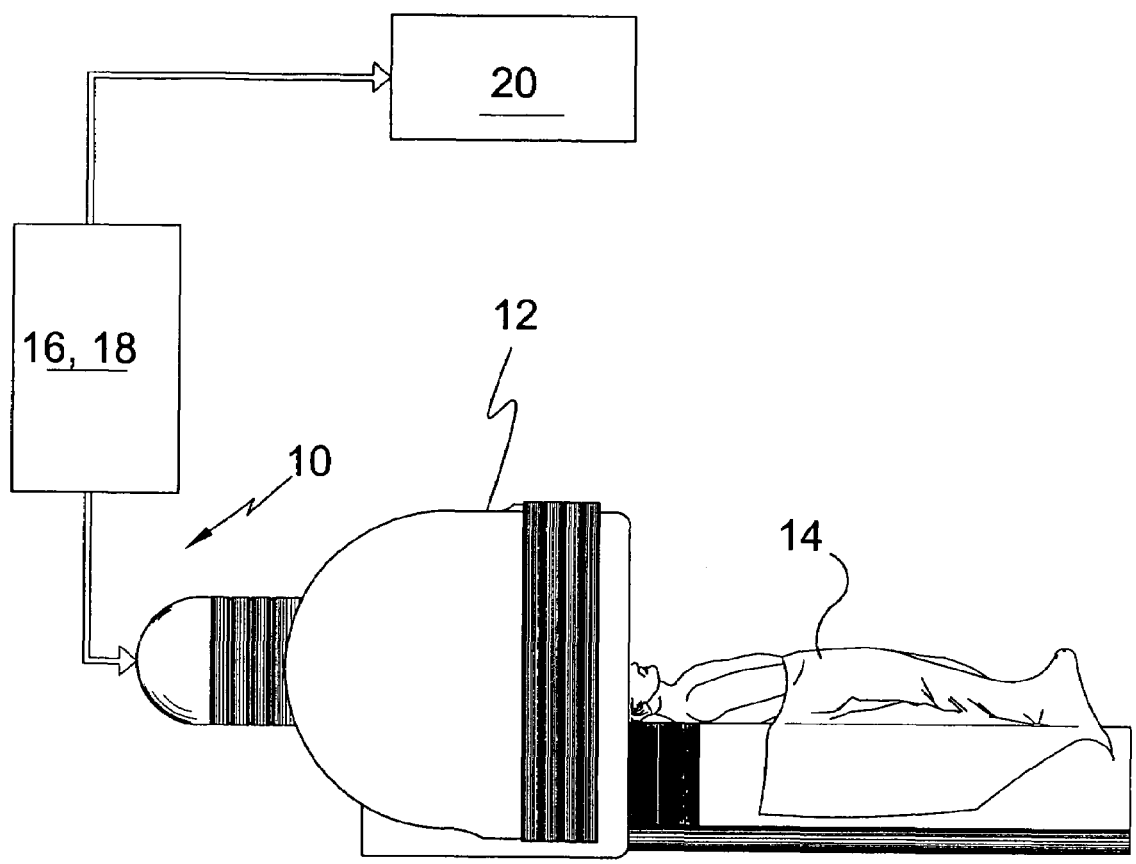
FIG. 1 is an illustrative view of the visual inspection device for a gamma system of the present invention in use.

Turning descriptively to the drawings, in which similar reference characters denote similar elements throughout the several views, the Figures illustrate the gamma system visual inspection device of the present invention. With regard to the reference numerals used, the following numbering is used throughout the various drawing Figures.

10 inspection device of the present invention
12 rotating gamma system
14 patient
16 video camera
18 lights
20 control area
22 mechanical indicator
24 electronic encoder
26 cover
28 securing strap
30 source carrier
32 collimator carrier
34 rotation monitor
36 rear portion of rotating gamma system
38 signal
40 operator
42 structure

DETAILED DESCRIPTION OF THE PREFERRED EMBODIMENT

The following discussion describes in detail one embodiment of the invention. This discussion should not be construed, however, as limiting the invention to those particular embodiments. Practitioners skilled in the art will recognize numerous other embodiments as well. For definition of the complete scope of the invention, the reader is directed to appended claims.

Turning now descriptively to the drawings, in which similar reference characters denote similar elements throughout the several views, FIGS. 1 through 7 illustrate a cellular phone cradle of the present invention which is indicated generally by the reference numeral 10.

FIG. 1 is an illustrative view of the gamma system visual inspection device 10 of the present invention in use. The gamma system visual inspection device 10 includes a video camera 16 and at least one light 18. The light 18 can be any type of light source, including but not limited to an LED. The gamma system visual inspection device 10 is located within a rear portion 36 of a rotating gamma system 12 and mounted to a structure 42 therein, as shown hereinafter with specific reference to FIG. 3. The rotating gamma system 12 includes a source carrier 30 and a collimator carrier 32 that rotate independently of each other when the rotating gamma system 12 is in operation, as shown hereinafter with specific reference to FIG. 5. The rear portion 36 of the rotating gamma system 12 also includes an electronic encoder 24, shown hereinafter with specific reference to FIG. 2. The electronic encoder 24 electronically tracks the position of the source carrier 30 and the collimator carrier 32. The rear portion 36 of the rotating gamma system 12 also includes a mechanical indicator 22, shown hereinafter with specific reference to FIG. 2. The mechanical indicator 22 shows the physical positions of the source carrier 30 and the collimator carrier 32. The video camera 16 and the light 18 are trained on the mechanical indicator 22. The video camera 16 transmits a signal 38 representing the video data to a control area 20, where it is observed and monitored by an operator 40, not shown. The signal 38 can be transmitted either through wires or wirelessly. The signal 38 can be observed by plurality of means including but not limited to a live video monitor and a video capture computer. Additionally, in an alternative embodiment, a recording system is included to record the signal 38 for subsequent review.

The rotating gamma system 12 is an instrument for performing radiosurgery on lesions in the brain, and possibly other body parts. When the rotating gamma system 12 is in operation, the source carrier 30 and the collimator carrier 32 rotate independently, and a high concentration of radiation is sent to a very localized area of a patient 14. The rotational positions of the source carrier 30 and the collimator carrier 32 are precisely controlled and monitored electronically. The electronic encoder 24 tracks the position of the source carrier 30 and the collimator carrier 32. The mechanical indicator 22 shows the physical positions of the source carrier 30 and the collimator carrier 32. If there is an indexing error for the electronic monitors, visual inspection of the mechanical indicator 22 may show the error. However, the rotating gamma system 12 is operated from the control area 20 due to the radiation that is used and thus as the prior art system shows, the mechanical indicator 22 cannot be viewed. The video camera 16 and the light 18 of the gamma system visual inspection device 10 are trained on the mechanical indicator 22, thereby enabling the operator 40 to observe the mechanical indicator 22 for errors. The ability to observe the mechanical indicator 22 is an additional safety feature that enables the operator 40 to make sure the rotating gamma system 12 is operating properly.

Figure 2:
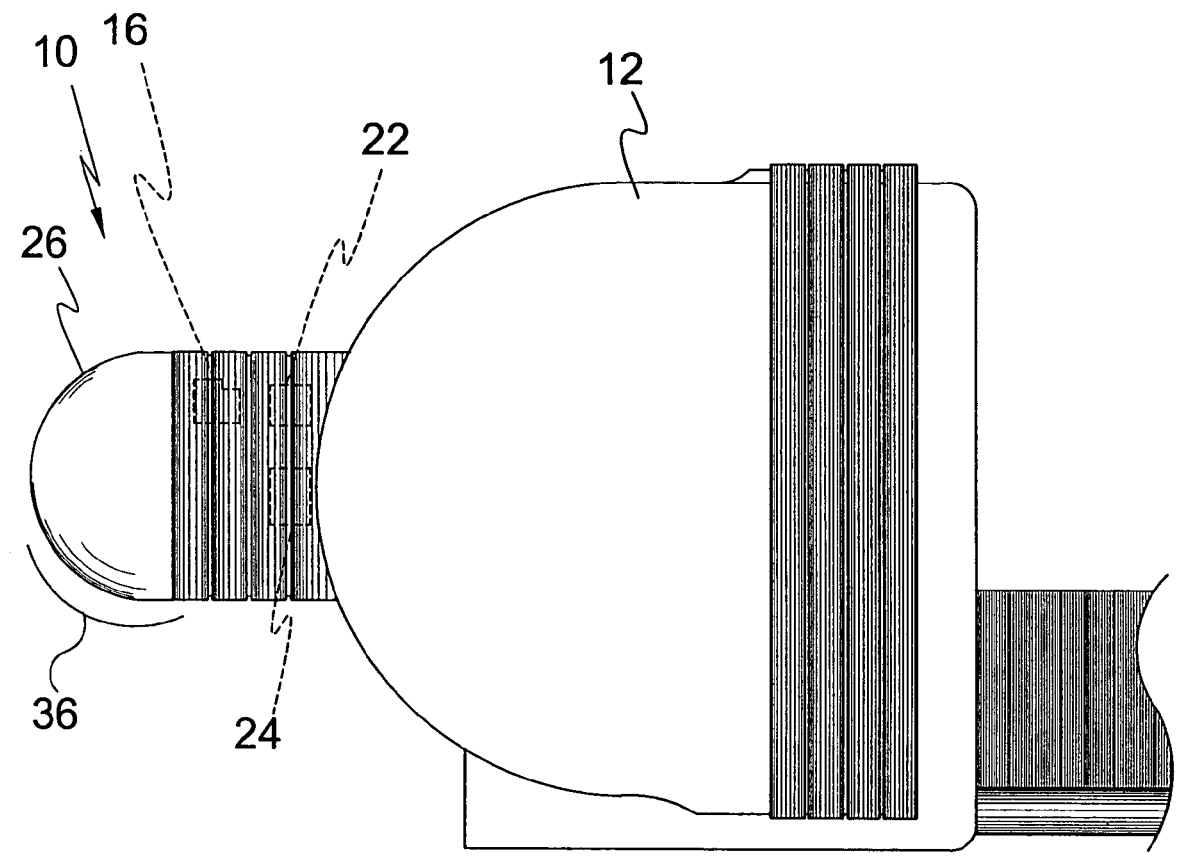
FIG. 2 is a side view of the visual inspection device for a gamma system of the present invention.

FIG. 2 is a side view of the gamma system visual inspection device of the present invention. The gamma system visual inspection device 10 includes the video camera 16 and at least one light 18. The gamma system visual inspection device 10 is located within the rear portion 36 of the rotating gamma system 12 and mounted to the structure 42 therein, as shown hereinafter with specific reference to FIG. 3. A cover 26 covers the rear portion 36 of the rotating gamma system 12. The source carrier 30 and the collimator carrier 32 are included in the rotating gamma system 12 and they rotate independently of each other when the rotating gamma system 12 is in operation, as shown hereinafter with specific reference to FIG. 5. The electronic encoder 24 is also included within the rear portion 36 of the rotating gamma system 12. The electronic encoder 24 electronically tracks the position of the source carrier 30 and the collimator carrier 32. The mechanical indicator 22 is also located within the rear portion 36 of the rotating gamma system 12. The mechanical indicator 22 shows the physical positions of the source carrier 30 and the collimator carrier 32. The mechanical indicator 22 shows any indexing errors that occur during the electronic monitoring. The video camera 16 and the light 18 are trained on the mechanical indicator 22. The video camera 16 transmits the signal 38 representing the video data to the control area 20, shown in FIG. 4, where it is observed and monitored by the operator 40, not shown.

Figure 3:
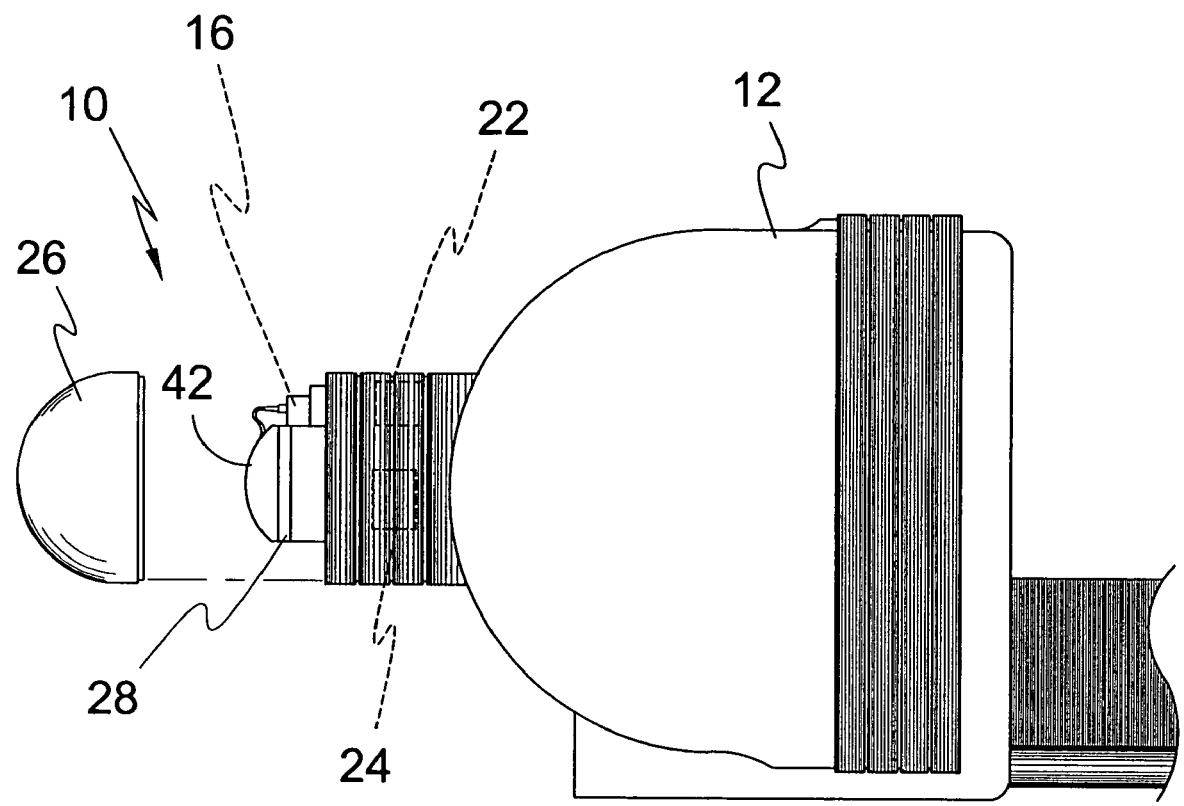
FIG. 3 is a side view of the visual inspection device for a gamma system of the present invention within the rear portion of the rotating gamma system.

FIG. 3 is a side view of the gamma system visual inspection device 10 of the present invention within the rear portion 36 of the rotating gamma system 12. The gamma system visual inspection device 10 includes the video camera 16 and at least one light 18. The gamma system visual inspection device 10 is located within the rear portion 36 of the rotating gamma system 12 and secured to the structure 42 therein by a securing strap 28. However, this is for purposes of example only, and any means for securing the gamma system visual inspection device 10 to the structure 42 may be used. These securing means include but are not limited to the securing strap 28, an adhesive, hook and loop tape, snaps and a magnetic force. The cover 26 covers the rear portion 36 of the rotating gamma system 12. The source carrier 30 and the collimator carrier 32 are included in the rotating gamma system 12 and they rotate independently of each other when the rotating gamma system 12 is in operation, as shown hereinafter with specific reference to FIG. 5. The electronic encoder 24 is also included within the rear portion 36 of the rotating gamma system 12. The electronic encoder 24 electronically tracks the position of the source carrier 30 and the collimator carrier 32. The mechanical indicator 22 is also located within the rear portion 36 of the rotating gamma system 12. The mechanical indicator 22 shows the physical positions of the source carrier 30 and the collimator carrier 32. The mechanical indicator 22 shows any indexing errors that occur during the electronic monitoring. The video camera 16 and the light 18 are trained on the mechanical indicator 22. The video camera 16 transmits the signal 38 representing the video data to the control area 20, shown in FIG. 4, where it is observed and monitored by the operator 40, not shown.

Figure 4:
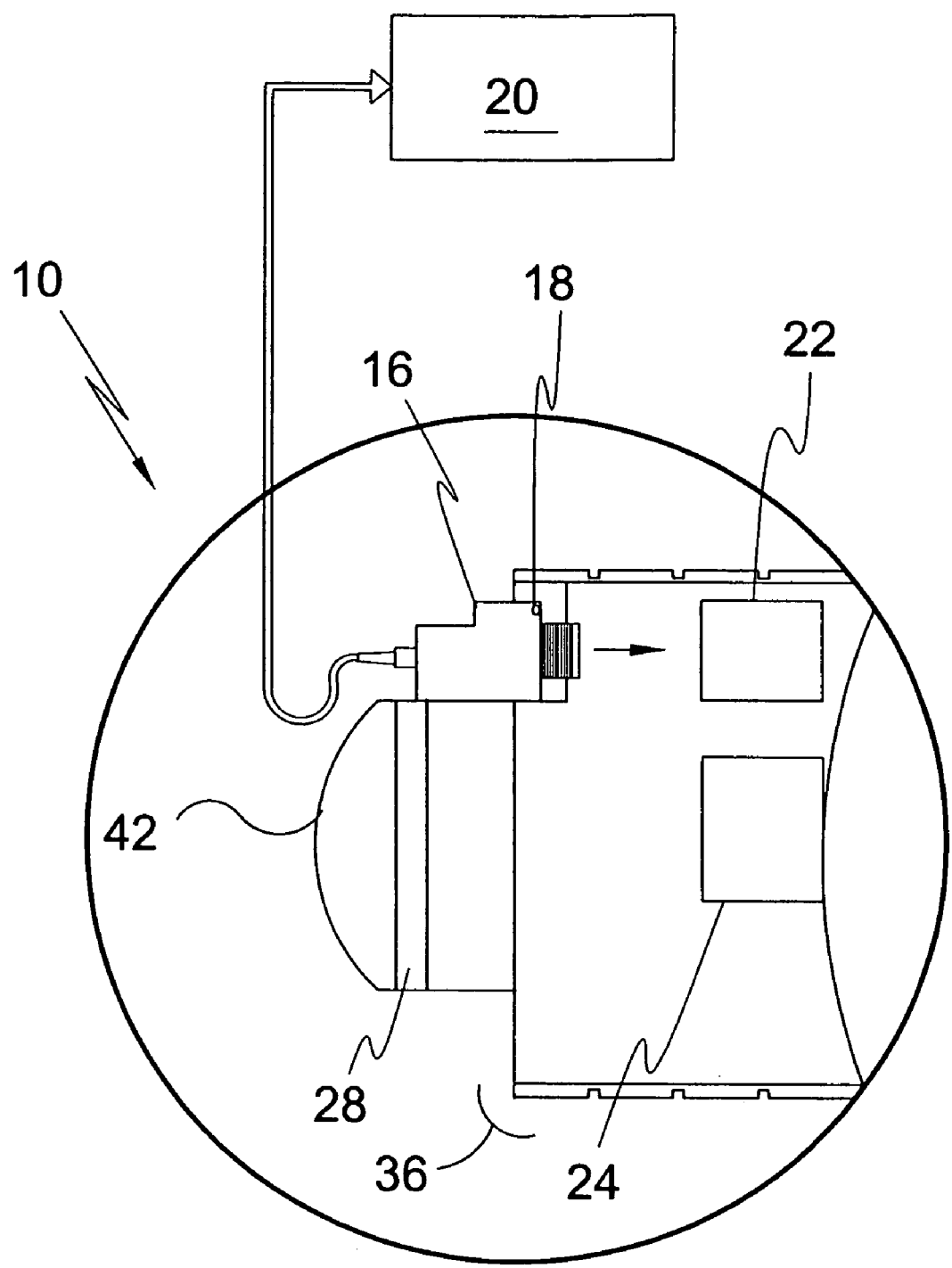
FIG. 4 is an illustrative view of the visual inspection device for a gamma system of the present invention within the rear portion of the rotating gamma system.

FIG. 4 is an illustrative view of the gamma system visual inspection device 10 of the present invention within the rear portion 36 of the rotating gamma system 12. The gamma system visual inspection device 10 includes the video camera 16 and at least one light 18. The gamma system visual inspection device 10 is located within the rear portion 36 of the rotating gamma system 12 and secured to the structure 42 therein by the securing strap 28. The source carrier 30 and the collimator carrier 32 are included in the rotating gamma system 12 and they rotate independently of each other when the rotating gamma system 12 is in operation, as shown hereinafter with specific reference to FIG. 5. The electronic encoder 24 is also included within the rear portion 36 of the rotating gamma system 12. The electronic encoder 24 electronically tracks the position of the source carrier 30 and the collimator carrier 32. The mechanical indicator 22 is also located within the rear portion 36 of the rotating gamma system 12. The mechanical indicator 22 shows the physical positions of the source carrier 30 and the collimator carrier 32. The mechanical indicator 22 shows any indexing errors that occur during the electronic monitoring. The video camera 16 and the light 18 are trained on the mechanical indicator 22. The video camera 16 transmits the signal 38 representing the video data to the control area 20, where it is observed and monitored by the operator 40, not shown.

Figure 5:
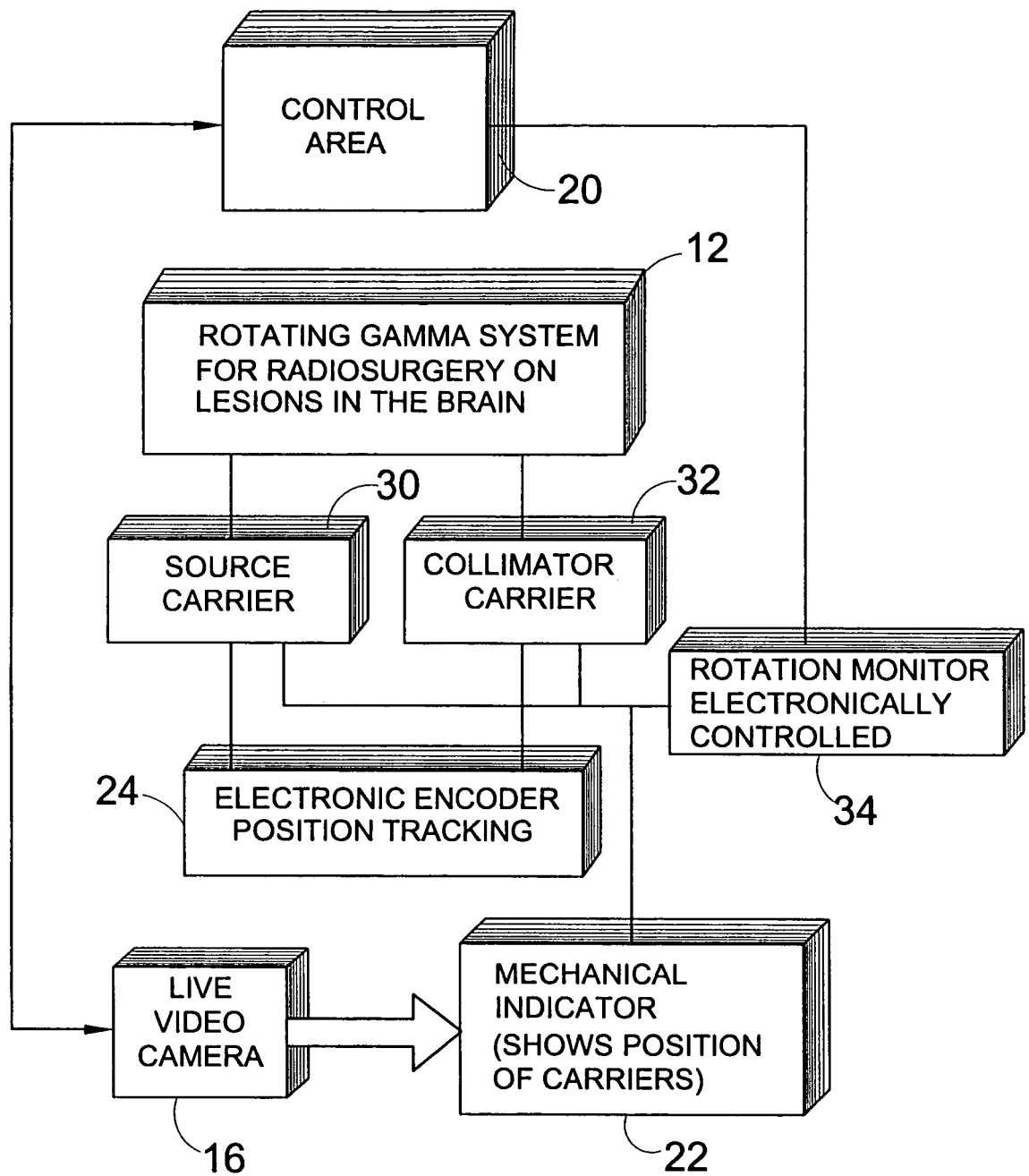
FIG. 5 is a block diagram of the visual inspection device for a gamma system of the present invention.

FIG. 5 is a block diagram of the gamma system visual inspection device 10 of the present invention. The rotating gamma system 12 is used to perform radiosurgery on lesions in the brains of patients 14 as well as in other medical procedures. The source carrier 30 and the collimator carrier 32 are located within the rotating gamma system 12 and rotate independently of one another. The rotation of the source carrier 30 and the collimator carrier 32 is electronically controlled by a rotation monitor 34, which is operated by the operator 40 in the control area 20. The electronic encoder 24 electronically tracks the positions of the source carrier 30 and the collimator carrier 32. The mechanical indicator 22 shows the physical position of the source carrier 30 and the collimator carrier 32. The mechanical indicator 22 shows any indexing errors that occur during the electronic monitoring. The video camera 16 takes live video of the mechanical indicator 22 and sends that information to the control area 20 where it can be observed and monitored by the operator 40, not shown.

Figure 6:
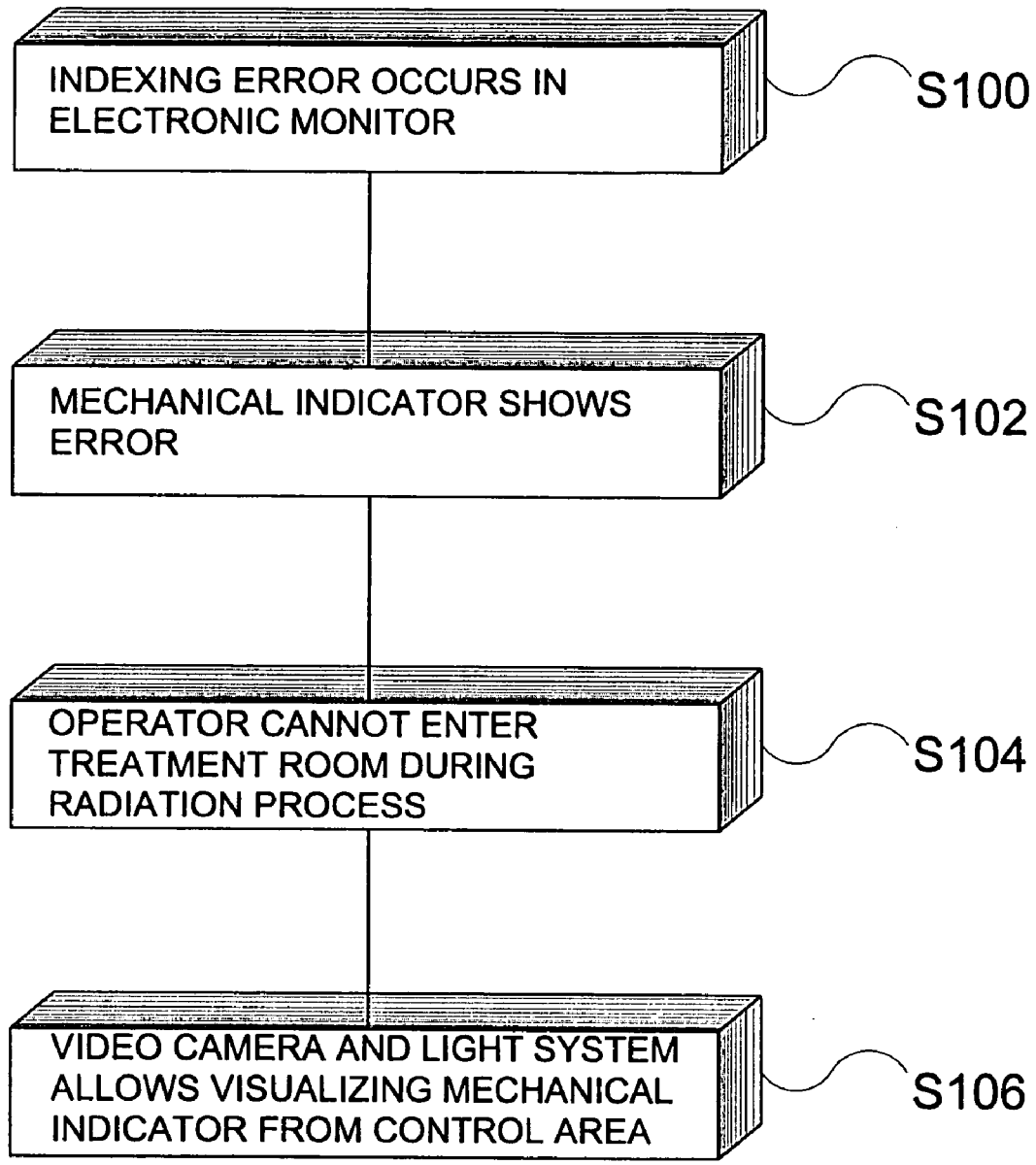
FIG. 6 is a flow diagram of the visual inspection device for a gamma system of the present invention.

FIG. 6 is a flow diagram of the gamma system visual inspection device 10 of the present invention. In step S100 an indexing error occurs in the electronic monitor. In step S102, the mechanical indicator 22 shows the indexing error. However, as shown in step S104, the operator 40 cannot enter the treatment room during the operation of the rotating gamma system 12 due to the radiation that is applied to the patient 14. In step S106, the video camera 16 and the lights 18 of the gamma system visual inspection device 10 provide a visual picture of the mechanical indicator 22 in the control area 20.

Figure 7:
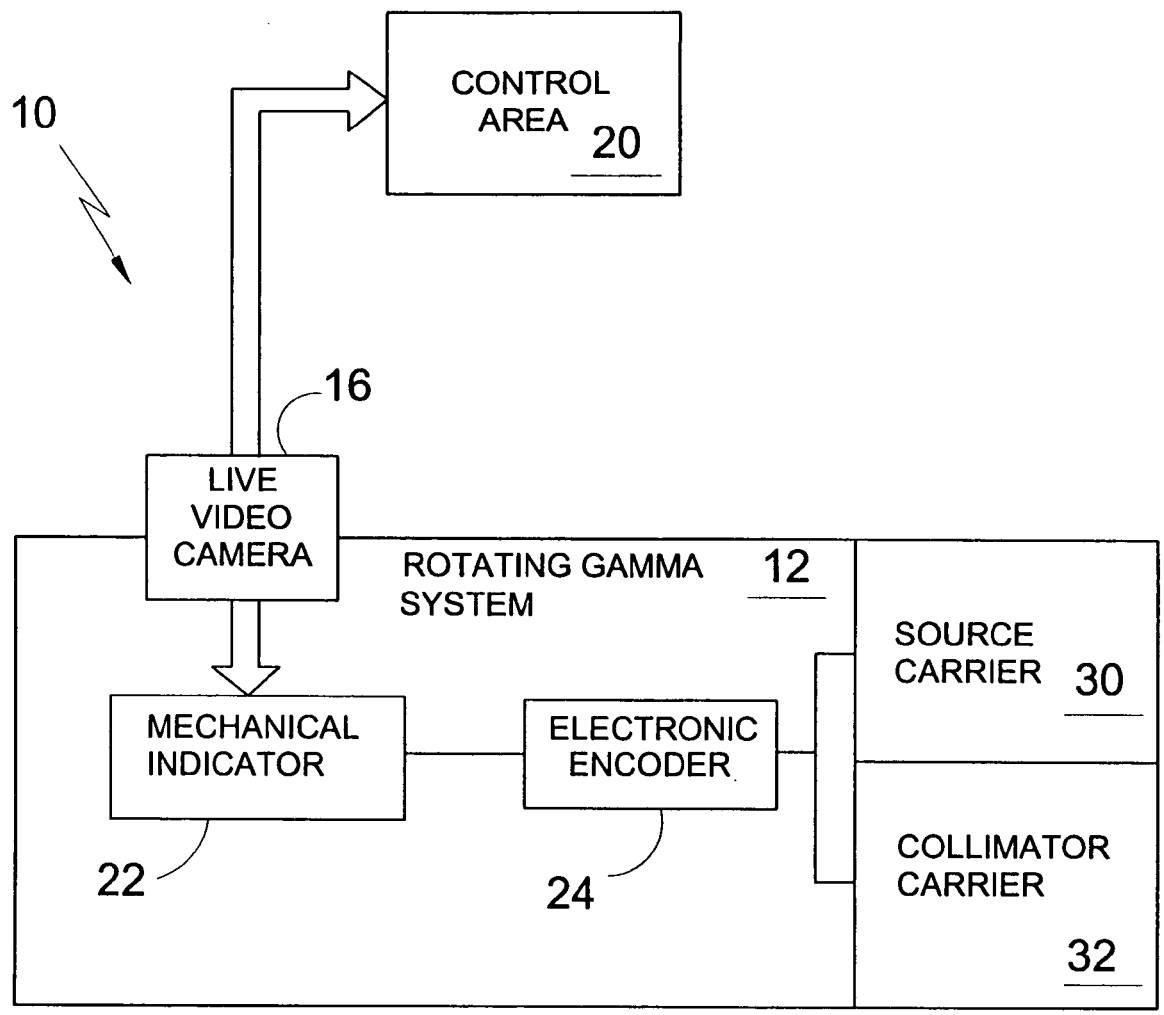
FIG. 7 is a block diagram of the visual inspection device for a gamma system of the present invention.

FIG. 7 is a block diagram of the gamma system visual inspection device 10 of the present invention. The rotating gamma system 12 is used to perform radiosurgery on lesions in the brains of patients 14 as well as in other medical procedures. The source carrier 30 and the collimator carrier 32 are located within the rotating gamma system 12 and rotate independently of one another. The rotation of the source carrier 30 and the collimator carrier 32 is electronically controlled by a rotation monitor 34, which is operated by the operator 40 in the control area 20, shown hereinabove with specific reference to FIG. 5. The electronic encoder 24 electronically tracks the positions of the source carrier 30 and the collimator carrier 32. The mechanical indicator 22 shows the physical position of the source carrier 30 and the collimator carrier 32. The mechanical indicator 22 shows any indexing errors that occur during the electronic monitoring. The video camera 16 takes live video of the mechanical indicator 22 and sends that information to the control area 20 where it can be observed and monitored by the operator 40, not shown.

It will be understood that each of the elements described above, or two or more together may also find a useful application in other types of devices differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by letters Patent is set forth in the appended claims:

1. A visual inspection device for use with a gamma system comprising:
   a. a rotating gamma system within a housing for performing radiosurgery with an opening at a front side of said housing for receiving a head of a patient, said housing having a rear portion with a removable cover;
   b. a visual inspection device within said rear portion comprising a video camera, a light, a rotating source carrier and a rotating collimator carrier;
   c. said rotating gamma system having an electronic coder tracking positions of said source carrier and collimator carrier;
   d. a mechanical indicator in said rear portion for showing physical positions of said source carrier and collimator carrier;
   e. said video camera and light being trained on said mechanical indicator and producing live video position data and sending said video position data to a remote control center for observation and monitoring; and
   f. a communication device connected between said camera and said control center for providing captured live video position data to said control center, wherein upon display of said captured data a user is able to review, monitor and maintain operation of the gamma system, identifying any indexing errors.

2. The device as recited in claim 1 wherein said captured data is at least one of a still image of the mechanical indicator and real-time video data of the mechanical indicator.

3. The device as recited in claim 2, wherein said camera is responsive to user control for capturing at least one of still image and real-time video data at predetermined time intervals.

4. The device as recited in claim 1, wherein said communication device is at least one of a wired network and a wireless network.

5. The device as recited in claim 1, wherein said communication device is internet compatible for providing said captured data via a wide area network a remote user.

6. The device as recited in claim 1, wherein said camera is selectively connected within the gamma system by at least one of a securing strap; an adhesive; book and loop tape; snaps and magnetic force.

7. A method for ensuring intended operation of a gamma system performing radiosurgery comprising the steps of:
   a. providing a camera within a housing of a gamma system proximate to a mechanical indicator thereof, said mechanical indicator showing physical positions of a rotating source carrier and a rotating collimator carrier tracked by an electronic coder;
   b. capturing positional data via the camera associated with the mechanical indicator;
   c. communicating via a communication device the captured data to a remote control center; and
   d. monitoring, in response to user command, the captured data to ensure that the gamma system is operating as intended while performing said radiosurgery.

8. The method as recited in claim 7, wherein said captured data is at least one of a plurality of still images of the mechanical indicator and real-time video data of the mechanical indicator.

9. The method as recited in claim 8, wherein communicating is performed over at least one of local area network and a wide area network.

10. The method as recited in claim 8, wherein said communicating is performed using one of a wired network and a wireless network.

* * * * *